United States Patent
Castel et al.

(10) Patent No.: US 8,881,894 B2
(45) Date of Patent: Nov. 11, 2014

(54) MULTIPLE-COMPARTMENT APPLICATOR

(75) Inventors: John C. Castel, Reno, NV (US); R. Patrick Abergel, Santa Monica, CA (US)

(73) Assignee: Sonovia Holdings LLC, Reno, NV (US)

( * ) Notice: Subject to any disclaimer, the term of this patent is extended or adjusted under 35 U.S.C. 154(b) by 1456 days.

(21) Appl. No.: 12/195,788

(22) Filed: Aug. 21, 2008

(65) Prior Publication Data

US 2010/0047326 A1    Feb. 25, 2010

(51) Int. Cl.
| | | |
|---|---|---|
| *B65D 25/08* | (2006.01) | |
| *B65D 1/09* | (2006.01) | |
| *A61K 9/70* | (2006.01) | |
| *A61K 31/375* | (2006.01) | |

(52) U.S. Cl.
CPC ............ *A61K 9/7023* (2013.01); *A61K 31/375* (2013.01)
USPC ............................ 206/219; 206/222; 206/528

(58) Field of Classification Search
USPC .................. 206/219–222, 528; 220/712–714, 220/145.5–145.6; 424/449; 514/474; 604/410, 416, 87
See application file for complete search history.

(56) References Cited

U.S. PATENT DOCUMENTS

| | | |
|---|---|---|
| 3,294,227 A | 12/1966 | Schneider et al. |
| 3,608,709 A | 9/1971 | Pike |
| 3,756,389 A | 9/1973 | Firth |
| 3,759,259 A | 9/1973 | Truhan |
| 3,958,571 A | 5/1976 | Bennington |
| 4,602,910 A | 7/1986 | Larkin |
| 4,740,194 A | 4/1988 | Barabino et al. |
| 4,778,457 A | 10/1988 | York |
| 4,784,506 A | 11/1988 | Koreska et al. |
| 4,790,839 A * | 12/1988 | Ahr ............................... 604/367 |
| 4,799,815 A | 1/1989 | Barabino et al. |
| 4,812,067 A | 3/1989 | Brown et al. |
| 4,983,382 A | 1/1991 | Wilmott et al. |
| 5,140,043 A | 8/1992 | Darr et al. |
| 5,287,961 A | 2/1994 | Herran |
| 5,458,244 A | 10/1995 | Emori |
| 5,490,736 A | 2/1996 | Haber et al. |
| 5,558,874 A | 9/1996 | Haber et al. |
| 5,568,988 A | 10/1996 | Knox et al. |
| 5,616,337 A | 4/1997 | Kasianovitz et al. |

(Continued)

FOREIGN PATENT DOCUMENTS

| | | |
|---|---|---|
| DE | 29 20 213 | 11/1980 |
| EP | 0 553 534 | 8/1992 |

(Continued)

OTHER PUBLICATIONS

International Search Report and Written Opinion dated Oct. 8, 2009 for PCT/US2009/004763; 13 pages.

*Primary Examiner* — Anthony Stashick
*Assistant Examiner* — Kaushikkumar Desai
(74) *Attorney, Agent, or Firm* — Stinson Leonard Street LLP

(57) ABSTRACT

A multiple-compartment ascorbic acid delivery unit is provided. The first compartment is impermeable to oxygen and ultraviolet light and contains a solid vitamin-containing composition comprising ascorbic acid or its pharmaceutically acceptable salts and esters. The second compartment is liquid impermeable and contains a pharmaceutically acceptable carrier system. The first compartment is entirely enclosed within said second compartment or vice versa. An opening is formed in the inner compartment in order to combine the contents of the two compartments to form an ascorbic acid carrier composition prior to delivery to the patient.

36 Claims, 3 Drawing Sheets

(56) References Cited

U.S. PATENT DOCUMENTS

| | | |
|---|---|---|
| 5,681,574 A | 10/1997 | Haber et al. |
| 5,804,213 A | 9/1998 | Rolf |
| 5,902,591 A | 5/1999 | Herstein |
| 5,935,584 A | 8/1999 | Guerrero et al. |
| 6,007,264 A | 12/1999 | Koptis |
| 6,036,887 A | 3/2000 | Guerin et al. |
| 6,180,133 B1 | 1/2001 | Quan et al. |
| 6,299,798 B1 | 10/2001 | Guerin et al. |
| 6,361,783 B2 | 3/2002 | Moaddel et al. |
| 6,503,013 B2 | 1/2003 | Strauss |
| 6,547,468 B2 | 4/2003 | Gruenbacher et al. |
| 6,695,515 B1 | 2/2004 | Fleury |
| 6,811,338 B1 | 11/2004 | Manske, Jr. et al. |
| 6,902,335 B2 | 6/2005 | Bergey et al. |
| 6,945,402 B1 * | 9/2005 | Gueret ................ 206/581 |
| 7,186,046 B2 | 3/2007 | Kauffmann et al. |
| 2001/0008031 A1 | 7/2001 | Schultz et al. |
| 2002/0054857 A1 | 5/2002 | Shuch et al. |
| 2004/0062759 A1 * | 4/2004 | Abraham et al. ........... 424/94.1 |
| 2004/0109830 A1 | 6/2004 | Cashman et al. |
| 2005/0003725 A1 * | 1/2005 | Hill et al. ................ 442/123 |
| 2005/0152955 A1 * | 7/2005 | Akhave et al. ............ 424/445 |
| 2007/0078119 A1 | 4/2007 | Purro et al. |
| 2007/0119862 A1 | 5/2007 | Backes et al. |
| 2007/0223988 A1 | 9/2007 | Gruenbacher et al. |
| 2008/0033027 A1 | 2/2008 | Bascomb et al. |
| 2008/0057007 A1 | 3/2008 | Leonhardt et al. |

FOREIGN PATENT DOCUMENTS

| | | |
|---|---|---|
| WO | WO 97/06076 | 2/1997 |
| WO | WO 98/34581 | 8/1998 |
| WO | WO 00/09016 | 2/2000 |
| WO | WO 00/26280 | 5/2000 |
| WO | WO 01/17390 | 3/2001 |

* cited by examiner

MULTIPLE-COMPARTMENT APPLICATOR

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention relates to an applicator and method for the delivery of Vitamin C (ascorbic acid), especially for the topical delivery to a patient's skin. More particularly, the present invention relates to a multiple-compartment transdermal drug delivery device and delivery method for ascorbic acid in which a first compartment and a second compartment are concentrically located. One compartment houses a dry powder form of ascorbic acid, and the second compartment houses a solution or other suitable carrier. Just prior to use, the contents of the two compartments are mixed together, thus maintaining maximum efficacy of the ascorbic acid when applied to the skin surface.

2. Description of Related Art

The present invention relates to a device for the topical or transdermal delivery of Vitamin C (ascorbic acid) and its pharmaceutically acceptable salts and esters. Ascorbic acid has many known biological functions from enzymatic co-factor to "sparing" agent against Vitamin E depletion. The latter function may partly account for its "antioxidant" status. Additionally, at higher concentrations, ascorbic acid is known to react with both superoxide and hydroxyl radicals. Superoxide and the subsequently generated hydrogen peroxide and hydroxyl radical are oxygen-containing free radicals now known to be generated in vivo under a variety of normal and pathological conditions. Quite simply, these radicals have been implicated as causative agents for everything from sunburn to aging. These radicals destroy lipid membranes, breakdown DNA, inactivate enzymes, and so forth.

Ascorbic acid is also thought to be involved in wound healing. The process of wound healing generally encompasses three phases during which the injured tissue is repaired, regenerated, and new tissue is reorganized into a scar. These three phases are classified as: (a) an inflammation phase which begins from about day 0 to 3 days, (b) a cellular proliferation phase from about 3 to 12 days, and (c) a remodeling phase from about 3 days to about 6 months. In all three phases, antioxidants, such as Vitamin C, play a vital role in the healing process.

In the inflammation phase, inflammatory cells, mostly neutrophils, enter the site of the wound followed by lymphocytes, monocytes, and later macrophages. The neutrophils that are stimulated begin to release proteases and reactive oxygen species into the surrounding medium with potential adverse effects on both the adjacent tissues and the invading microorganisms.

The proliferative phase consists of laying down new granulation tissue, and the formation of new blood vessels in the injured area. The fibroblasts, endothelial cells, and epithelial cells migrate in the wound site. These fibroblasts produce the collagen that is necessary for wound repair. Ascorbic acid is crucial in the formation of collagen. Several studies have demonstrated that ascorbic acid was capable of overcoming the reduced proliferative capacity of elderly dermal fibroblasts, as well as increasing collagen synthesis in elderly cells by similar degrees as in newborn cells even though the basal levels of collagen synthesis are age dependent. A decrease of ascorbic acid at the injury area will decrease the rate of wound healing.

In reepithelialization, epithelial cells migrate from the free edges of the tissue across the wound. This event is succeeded by the proliferation of epithelial cells at the periphery of the wound. Research has also shown that reepithelialization is enhanced by the presence of occlusive wound dressings which maintain a moisture barrier.

The final phase of wound healing, which is remodeling, is effected by both the replacement of granulation tissue with collagen and elastin fibers and the devascularization of the granulation tissue. Recent studies have shown that topical application of antioxidants reduces scarring and normalizes blood coagulation during therapy.

L-Ascorbic acid is chemically defined as an alpha-ketolactone and containing an acid-ionizable hydrogen in water (pK=4.2). Ascorbic acid is also a moderately strong reductant. These properties, which lead to instability in the ascorbic acid structure, are well known and have been burdensome to pharmacologists when attempting to formulate active ascorbic acid solutions. Thus, at higher pHs values, the ascorbic acid increasingly becomes the notoriously unstable ascorbate anion. This instability may be due to several causes not restricted to stereochemical strain, oxidative degradation, and degradation due to water attack.

For these reasons, among others, scientists working in the field have had difficulty in formulating stable solutions of ascorbic acid which would be useful for cosmetic or dermatological needs. Nevertheless, because of the many beneficial pharmaceutical effects attributed to ascorbic acid, numerous attempts have been made to overcome these difficulties.

BRIEF SUMMARY OF THE INVENTION

The present invention is directed to a multiple-compartment ascorbic acid delivery unit and methods of using the multiple-compartment delivery unit to deliver ascorbic acid to a surface, such as a patient's skin. The multiple-compartment delivery unit comprises at least two compartments. The first compartment contains a solid vitamin-containing composition comprising ascorbic acid or its pharmaceutically acceptable salts and esters. The first compartment is impermeable to oxygen and ultraviolet light. Preferred materials used to form the first compartment include, but are not limited to, a deformable metal or polymer, aluminized or metallized polymer, polycarbonate, polyethylene, vinyl, and polyethylene terephthalate polyester film. The first compartment may optionally contain other solid therapeutic agents, for example at least one additional antioxidant in addition to the ascorbic acid.

The second compartment contains a pharmaceutically acceptable carrier system. The second compartment is liquid impermeable, and is preferably made of a plastic film. Preferred pharmaceutically acceptable carrier systems include water, as well as one or more organic solvents miscible with water. In addition, the second compartment may optionally contain one or more therapeutic agents, chelators, or pH regulators. Exemplary therapeutic agents include antioxidants, growth factors, hormones, growth inhibitors, vitamins, exfoliators, skin toners, lubricants, hydrators, muscle relaxers, muscle toners, and skin protectors.

In the present invention, the first compartment is entirely enclosed within the second compartment or the second compartment is entirely enclosed within the first compartment. Thus the first compartment and the second compartment are concentrically located. The first compartment or second compartment has a means for combining the solid vitamin-containing composition and the pharmaceutically acceptable carrier system to form an ascorbic acid carrier composition.

In one aspect, the first compartment is an outer compartment containing a solid vitamin-containing composition comprising ascorbic acid or its pharmaceutically acceptable salts and esters. The outer compartment is impermeable to oxygen and ultraviolet light. The second compartment is an inner compartment enclosed within the outer compartment. The inner compartment contains a pharmaceutically acceptable carrier system and is liquid impermeable.

Alternatively, the first compartment is an inner compartment containing a solid vitamin-containing composition comprising ascorbic acid or its pharmaceutically acceptable salts and esters. The inner compartment is impermeable to oxygen and ultraviolet light. The second compartment is an outer compartment that enclosed the inner compartment. The inner compartment contains a pharmaceutically acceptable carrier system and is liquid impermeable.

In one aspect, the means for combining the solid vitamin-containing composition and the pharmaceutically acceptable carrier system to form an ascorbic acid carrier composition comprises a breakable barrier integrally formed in the inner compartment, such that when the breakable barrier is broken, the vitamin-containing composition and the pharmaceutically acceptable carrier system are capable of being combined to form an ascorbic acid carrier composition. Exemplary means for combining the contents of inner compartment and the outer compartment together include a declivity, score line, or frangible seal in the inner compartment. In one aspect, the delivery unit further comprises instructions printed on the outer compartment for applying pressure to the outer compartment at a predetermined location in order to break the breakable barrier.

In another aspect, the means for combining the solid vitamin-containing composition and the pharmaceutically acceptable carrier system to form an ascorbic acid carrier composition comprises the inner compartment being formed with scaled edges being capable of opening in response to a pressure exerted on a flexible wall of the outer compartment. For example, a width of a portion of the sealed edges of the inner compartment may be less than a sealed width of the other edges.

In still another aspect, the outer compartment of the ascorbic acid delivery unit of the present invention comprises a gated opening. The gated opening has an open position and a closed position. When the gated opening is in the open position, the ascorbic acid carrier composition can pass through the gated opening, and when the gated opening is in the closed position the ascorbic acid carrier composition remains confined within the outer compartment.

In yet a further aspect, the ascorbic acid delivery unit of the present invention includes an absorbent structure. The absorbent structure is selected from the group consisting of a woven material, a nonwoven material, an open-cell foam, a semi-open-cell foam, felt, and hydrogel, collagen, and hydrocolloid laminates. The absorbent structure may be any suitable shape or size for delivery of the ascorbic acid carrier composition, and is preferably selected from the group consisting of a wipe, a patch, a pad, and a mask. The absorbent structure may be enclosed within the outer compartment or coupled to the outer compartment. The absorbent structure may be enclosed within the inner compartment or coupled to the inner compartment. Thus, in one aspect, the absorbent structure may be coated and/or impregnated with the solid vitamin-containing composition comprising ascorbic acid or its pharmaceutically acceptable salts and esters.

In yet another aspect, the ascorbic acid delivery of the present invention includes an abrasive material. The abrasive material may be a separate structure or be coupled or adhered to the absorbent structure. Most preferably, the absorbent structure has an abrasive material on at least a portion of its surface or the abrasive material is impregnated within the absorbent structure.

In still another aspect, the outer compartment of the ascorbic acid delivery unit has a means for exposing the ascorbic acid carrier composition to the environment. For example, the outer compartment may have at least one tear notch, whereby the tear notch allows a user to tear away a portion of the outer compartment. As another example, the outer compartment may have a frangible seal formed in the outer compartment.

In yet a further aspect, the present invention takes the form of a multiple compartment ascorbic acid delivery kit. The kit comprises the combination of (1) a multiple-compartment ascorbic acid unit as described herein; and (2) a set of instructions for combining the contents of the first and second compartments together. For example, the instructions may direct the user to break the breakable barrier, mix the solid vitamin-containing composition and the pharmaceutically acceptable carrier system together to form an ascorbic acid carrier composition, and transfer the ascorbic acid carrier composition to an intended surface.

In one aspect, the multiple compartment ascorbic acid delivery kit comprises an absorbent material. The set of instructions preferably comprise directions to absorb the ascorbic acid carrier composition with the absorbent material in order to transfer the ascorbic acid carrier composition to the intended surface.

In yet another aspect, the multiple compartment ascorbic acid delivery kit comprises an abrasive material. The set of instructions further comprise directions to abrade the intended surface with the abrasive material prior to or simultaneous with the transfer of the ascorbic acid carrier composition to the intended surface.

The present invention is also directed to a method for delivering ascorbic acid to the skin of a subject in need thereof. The first step includes providing an ascorbic acid multiple-compartment unit as disclosed herein. The second step includes combining the solid vitamin-containing composition and the pharmaceutically acceptable carrier system together to form a ascorbic acid carrier composition, and the final step includes applying the ascorbic acid carrier composition to the skin. The method optionally includes the steps of abrading the patient's skin and/or applying the ascorbic acid carrier composition to the skin using an absorbent material.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 3A illustrates an exemplary declivity formed in the inner compartment. FIG. 3B illustrates an exemplary score line integrally formed in the inner compartment. FIG. 3C illustrates an exemplary frangible seal formed in the inner compartment.

DETAILED DESCRIPTION OF PREFERRED EMBODIMENT

The present invention is directed to a multiple-compartment ascorbic acid delivery device. The device is used to apply a therapeutic composition comprising ascorbic acid or its pharmaceutically acceptable salts and esters in a pharmaceutically acceptable carrier system, such as water and/or ethyl alcohol, to the skin. The device comprises a first compartment containing solid ascorbic acid and a second compartment containing a pharmaceutically acceptable carrier system such that one of the compartments is entirely located within the other compartment. In one aspect, the first compartment is the outer compartment such that the second compartment is disposed entirely within the first compartment. In another aspect, the second compartment is the outer compartment such that the first compartment is disposed entirely within the second compartment. The compartments contain a means for combining the contents of the inner and outer compartments together.

Figure 1A:
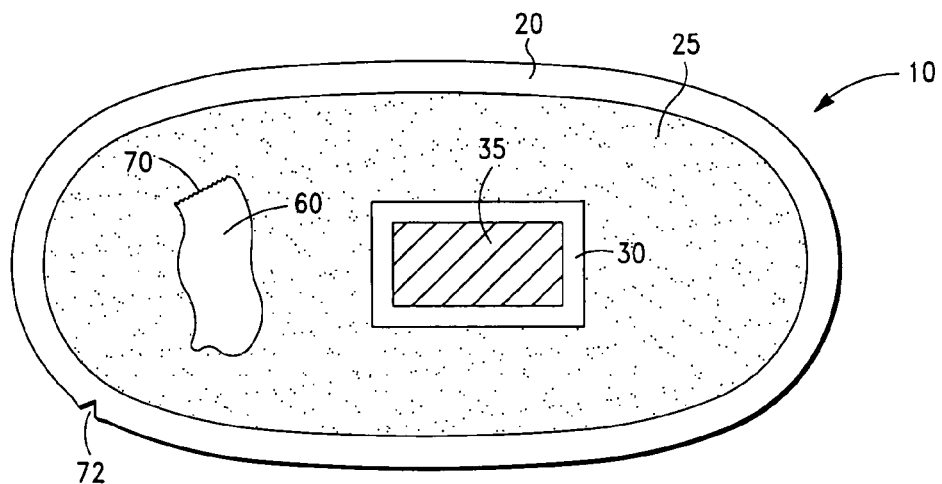
FIG. 1A illustrates the multiple compartment ascorbic acid delivery device in accordance with a first embodiment of the present invention. The solid vitamin containing composition comprising ascorbic acid is located in an outer compartment and a pharmaceutically acceptable carrier system is located in an inner compartment.

Turning now to the drawings, FIG. 1A illustrates the multiple-compartment ascorbic acid delivery device 10 in accordance with a first embodiment of the present invention. The device 10 comprises a first outer compartment 20 containing a solid vitamin-containing composition 25 comprising ascorbic acid or its pharmaceutically acceptable salts and esters. The material used to form the first outer compartment 20 is impermeable to oxygen and ultraviolet light. The device 10 further comprises a second inner compartment 30 containing a pharmaceutically acceptable carrier system 35. The inner compartment is comprised of a material that is liquid impermeable. While the compartments are generally illustrated in a rectangular shape, it will be appreciated that the outer compartment and the inner compartment may be any suitable shape (e.g., circular, elongated, and the like).

Figure 1B:
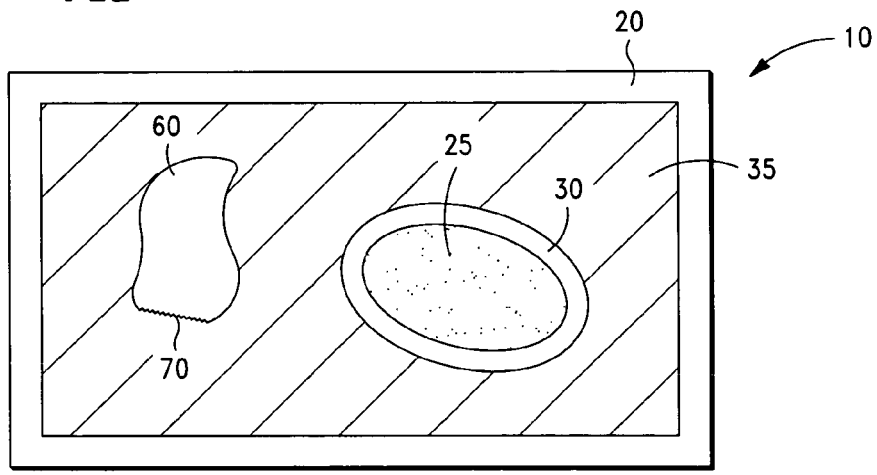
FIG. 1B illustrates the multiple compartment ascorbic acid delivery device in accordance with a second embodiment of the present invention. The solid vitamin containing composition comprising ascorbic acid is located in an inner compartment and a pharmaceutically acceptable carrier system is located in an outer compartment.

FIG. 1B illustrates the multiple compartment ascorbic acid delivery device in accordance with a second embodiment of the present invention. The second embodiment is similar to the first embodiment except that the solid vitamin containing composition comprising ascorbic acid is located in an inner compartment and a pharmaceutically acceptable carrier system is located in an outer compartment. The compartments are preferably full enough to cause an opening to form in the inner compartment when pressure is applied.

The compartment housing the solid vitamin-containing composition 25 comprising ascorbic acid or its pharmaceutically acceptable salts and esters is preferably comprised of a material selected from the group consisting of deformable metal or polymer. Exemplary oxygen impermeable materials that are also non-hydroscopic include "Mylar" sold by Dupont which is a polyethylene terephthalate polyester film, vinyl film, PE-paper colaminates, PE-foil, PE cellulose, biaxially oriented nylon, vinylidene chloride copolymer (saran), nylon, polyethylene terephthalate, ethylene/vinyl alcohol copolymer, and silicon oxides (SiOx). Solid pigments that reflect UV radiation, thus making a material UV impermeable include titanium dioxide, zinc oxide, zinc sulfide, and thiopene. Solid pigments that absorb UV radiation, thus making a material UV impermeable include carbon black. Materials that are inherently UV impermeable include aromatic hydrocarbons, hydrocarbons with extended portions of conjugated unsaturation, and metal foils (aluminum foil) aluminized or metallized polycarbonates, vinyls, and Mylar. The preferred materials are a deformable metal or polymer, aluminized or metallized polymer, polycarbonate, polyethylene, vinyl, and polyethylene terephthalate polyester film.

The compartment housing the carrier system 35 is preferably comprised of a material selected from the group consisting of plastic film. The material may be made of a multilayer complex, for example, of the thermoplastic/metal/thermoplastic or the polyethylene terephthalate/polyethylene/ceramic/polyethylene (PET/PE/SiO$_x$/PE) type, polycarbonate film and Mylar. The compartment may be made by heat-scaling together the edges by welding or applying an adhesive to the edges.

The vitamin-containing composition 25 comprising ascorbic acid or its pharmaceutically acceptable salts and esters in the first compartment 20 contains a therapeutically effective amount of ascorbic acid or its pharmaceutically acceptable salts and esters. A therapeutically effective amount of antioxidant is that amount of antioxidant necessary for the inventive composition to prevent and reduce injury to mammalian cells or increase the resuscitation rate of injured mammalian cells. The exact amount of antioxidant is a matter of preference subject to such factors as the type of condition being treated as well as the other ingredients or excipients in the composition. Typically, the vitamin-containing composition comprises about 200 to 800 milligrams of ascorbic acid, or its pharmaceutically acceptable salts or esters in the form of a crystalline powder. However, it is to be expressly understood that the ascorbic acid could also take the form of a dry medication wafer or other solid form, rather than a powder.

The solid vitamin-containing composition 25 may contain other solid therapeutic agents, such as antioxidants, growth factors, hormones, growth inhibitors, vitamins, exfoliators, skin toners, muscle relaxers, muscle toners, and skin protectors. Preferred therapeutics include collagen type I, alpha-tocopherol (vitamin E), and particulate starch hydrolysate that are applied on wounds to promote the formation and growth of healthy granulation tissue. In addition to ascorbic acid, the therapeutic composition may contain additional antioxidants. In general, antioxidants are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. The antioxidants useful in the present invention are preferably selected from the group consisting of: all forms of tea or its extracts including, black, red, and green tea, all forms of vitamin A (retinol, palmitate), all forms of vitamin $A_2$ (3,4-didehydroretinol), all forms of carotene such as alpha-carotene, beta-carotene, gamma-carotene, delta-carotene, all forms of vitamin C (D-ascorbic acid, L-ascorbic acid), all forms of tocopherol such as vitamin E (alpha-tocopherol, 3,4-dihydro-2,5,7,8-tetramethyl-2-(4,8,12-trimethyltri-decyl)-2H-1-benzopyran-6-ol), beta-tocopherol, gamma-tocopherol, delta-tocopherol, tocoquinone, tocotrienol, and vitamin E esters which readily undergo hydrolysis to vitamin E such as vitamin E acetate and vitamin E succinate, and pharmaceutically acceptable vitamin E salts such as vitamin E phosphate, prodrugs of vitamin A, carotene, and vitamin E, pharmaceutically acceptable salts of vitamin A, carotene, and vitamin E, and the like, and mixtures thereof. Preferably, the additional antioxidant is selected from the group of lipid-soluble antioxidants consisting of vitamin A, beta-carotene, vitamin E, vitamin E acetate, and mixtures thereof. Dosing of each of these agents is well known to those skilled in the art, and can be readily determined using standard techniques.

The pharmaceutically acceptable carrier system 35 in the second compartment 35 is preferably a liquid, cream, lotion, gel, or paste. The rheological properties of the carrier system 35 are such that the carrier system 35 can be readily mixed with the solid vitamin-containing composition 25, including by manually moving the carrier from one compartment to the other. In one embodiment, the carrier system preferably comprises water. The carrier system in the second compartment may optionally comprise one or more organic solvents miscible with water. There are many mono, di, or polyhydric liquids suitable for this purpose including, for example, alcohols, glycols, and polyols. Without limitation, one or more of the following organic solvents may be employed ethanol, N-propanol, isopropyl alcohol, methanol, propylene glycol, butylene glycol, hexylene glycol, glycerine, sorbitol (polyol), di-propylene glycol, and polypropylene glycol. The organic solvent may comprise up to about 90% by weight of the carrier system. See generally Wilmott et al., U.S. Pat. No. 4,983,382, which is incorporated by reference. In addition, other therapeutic agents, chelators, pH regulators, or carriers, may be dissolved, dispersed, or emulsified in the carrier system. See generally Darr et al., U.S. Pat. No. 5,140,143, which is incorporated by reference. Exemplary therapeutics are discussed above and include without limitation, growth agents, growth factors or hormones, growth inhibitors, scrums, treatment material, cleaners, vitamins, exfoliators, skin toners (peptides), lubricants (glycerol), hydrators (hyaluronic acid, jojoba and olive oils and their extracts, phyto squalan) muscle relaxers (argireline) or muscle toners (especially substances that stimulate neurotransmitter activation, e.g., nerve growth factors), substances which provide a protective skin film (tritisol, phytopeptides, hydrolyzed wheat protein, marine elastin and algae and derivatives) or other substances that can be used to treat a patient's skin.

In order to avoid obtaining a therapeutic composition which is too acidic (i.e., a pH less than 3.5) after introducing the ascorbic acid or its pharmaceutically acceptable salts and esters, it is preferable to add to the carrier system one or more pH-regulating agents. Examples of such agents include sodium citrate or sodium acetate buffer. The quantity of buffer is a function of the quantity of ascorbic acid used and the desired final pH; the latter is typically from 3.0 to 6, more preferably from 3.8 to 4.5 but including all values and all ranges there between.

Figure 2:
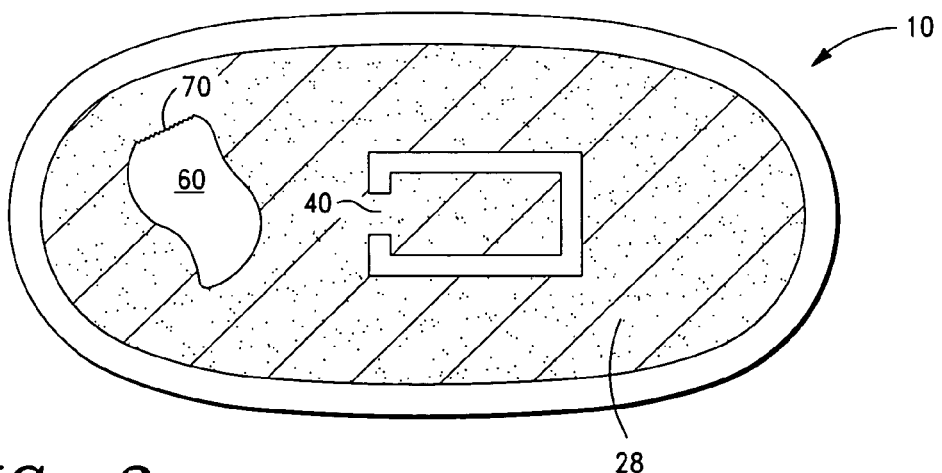
FIG. 2 illustrates the multiple compartment ascorbic delivery device in accordance with either the first or second embodiments. An opening is formed in the inner compartment, and the contents of the inner compartment and the outer compartment are combined to form an ascorbic acid carrier composition that can be topically applied to the patient's skin.

The inner and outer compartments 20, 30 have a means for combining the contents of the inner and outer compartments together. More specifically, an opening 40 is provided in the inner compartment such that the carrier system 35 in the inner compartment can be mixed with vitamin-containing composition 25 comprising ascorbic acid or its pharmaceutically acceptable salts and esters in order to form an ascorbic acid carrier composition 28 just prior to treatment (FIG. 2). Preferably, the ascorbic acid carrier composition 28 comprises about 2 wt. % and 35 wt. % ascorbic acid or its pharmaceutically acceptable salts and esters, and most preferably between about and 10 wt. % to 25 wt. % ascorbic acid or its pharmaceutically acceptable salts and esters, although other concentrations may be used based on the desired therapeutic effect. However, prior to use, the solid vitamin-containing composition 25 comprising ascorbic acid or its pharmaceutically acceptable salts and esters is separated from the carrier system 35.

Figure 3A:
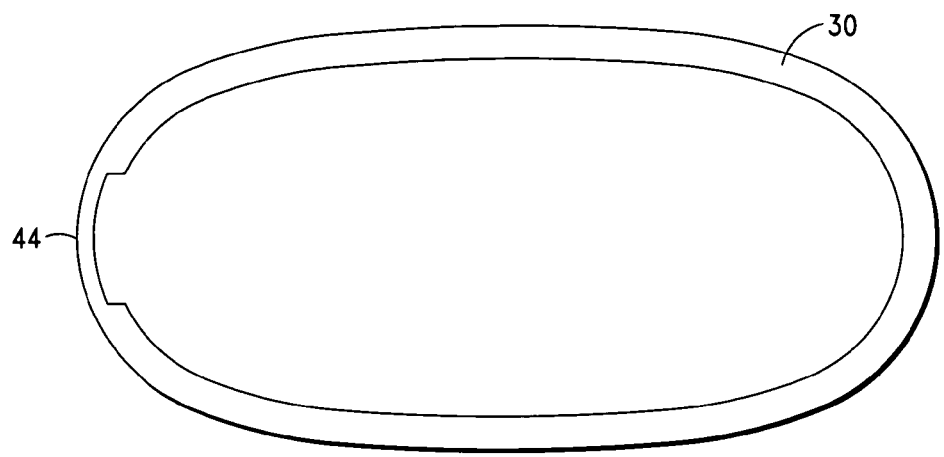
FIGS. 3A-3C show examples of a breakable barrier used to combine the contents of the inner and outer compartment.
Figure 3B:
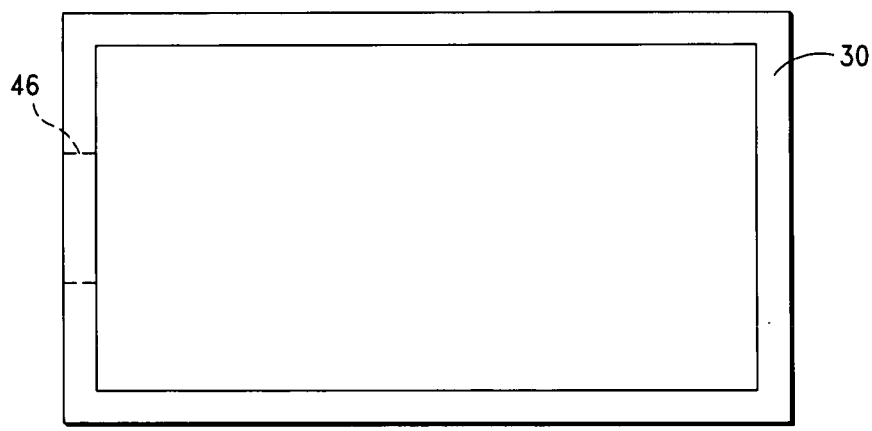
Figure 3C:
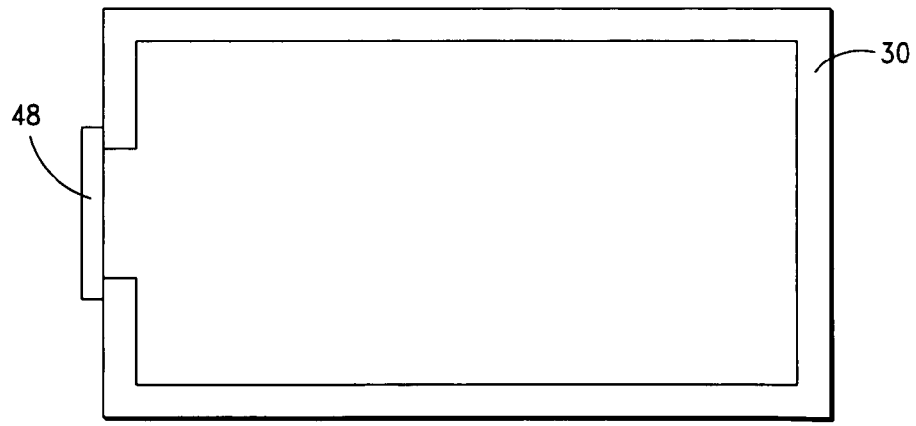

In one embodiment, as shown in FIGS. 3A-3C, the means for combining the solid vitamin-containing composition 25 comprising ascorbic acid or its pharmaceutically acceptable salts and esters with the carrier system 35 comprises a breakable barrier integrally formed in the inner compartment 30. When said breakable barrier is broken, an opening 40 is formed and the solid vitamin-containing composition 25 and the pharmaceutically acceptable carrier system 35 are capable of being combined to form an ascorbic acid carrier composition 28.

FIGS. 3A-3C show examples of a breakable barrier. More specifically, the breakable barrier may comprise a declivity 44 (FIG. 3A), score line 46 (FIG. 3B), or frangible seal 48 (FIG. 3C), or other zone of weakness in the inner compartment 30. Thus, when the inner compartment is bent, flexed, or compressed along the breakable barrier, an opening 40 is created in the inner compartment 30, permitting the contents of the inner compartment 30 and the outer compartment 20 to mix. Mixing may be facilitated by the user merely by shaking or moving the device, as well as by continuing to bend, flex, or compress the device. Other exemplary frangible seals are disclosed in Truhan, U.S. Pat. No. 3,759,259, which is incorporated by reference.

The outer compartment 20 may optionally have one or more markings corresponding to the breakable barrier so that the user may visualize where the bending, flexing, or compressing forces should be localized in order to create the opening in the inner compartment 30. The markings may comprise one or more instructions, such as "Bend Here" or may simply be a dot, line or other marking.

Figure 4A:
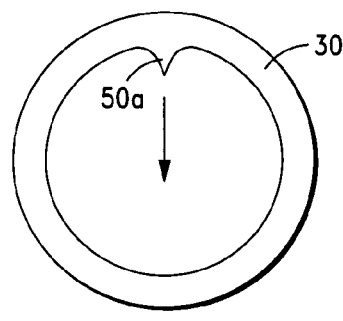
FIGS. 4A and 4B show puncture tips formed in the inner compartment for forming an opening in the inner compartment.
Figure 4B:
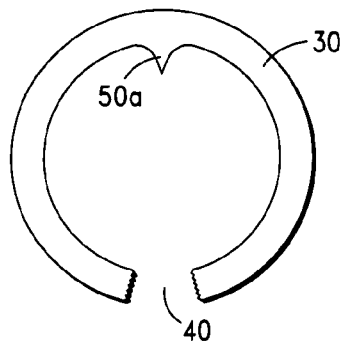

In another embodiment, as shown in FIG. 4A, one or more puncture tips 50a are provided along inner surface 32 of the inner compartment 30. When a compressive, bending, or flexing force is applied against the puncture tips 50a, the tips puncturely engage the opposite side of the inner compartment by moving them in the direction generally shown by the arrow (FIG. 4A), and form an opening 40 therein (FIG. 4B), permitting the contents of the first compartment and the second compartment to mix.

Figure 5A:
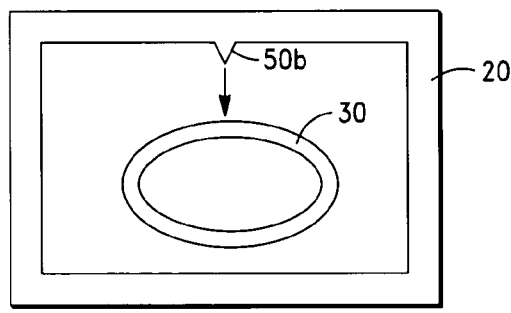
FIGS. 5A and 5B show puncture tips formed in the outer compartment for forming an opening in the inner compartment.
Figure 5B:
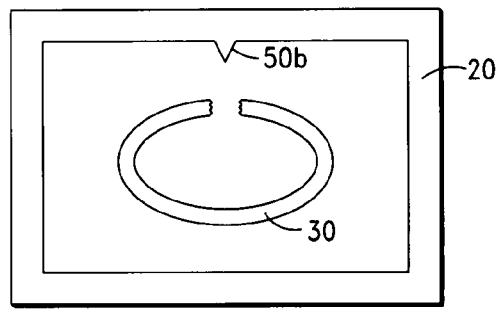

In still another embodiment, as shown in FIG. 5A, one or more puncture tips 50b are provided along inner surface 22 of the outer compartment 20. When a compressive, bending, or flexing force is applied against the puncture tips 50b, the tips puncturely engage the adjacent side of the inner compartment by moving them in the direction generally shown by the arrow (FIG. 5A), and form an opening therein (FIG. 5B), permitting the contents of the first compartment and the second compartment to mix.

The outer compartment 20 may optionally have one or more markings corresponding to the location of the puncture tips 50a, 50b so that the user may visualize where the bending, flexing, or compressing forces should be localized in order to create the opening in the inner compartment. The markings may comprise one or more instructions, such as "Bend Here" or may simply be a dot, line or other marking.

In still another embodiment, the means for combining comprises forming the inner compartment with scaled edges being capable of opening or rupturing in response to a pressure exerted on the inner compartment and its contents. Preferably, the width of a portion of the scaled edges of the inner compartment less than the scaled width of the other edges so as to localize where the opening will be made in response to the pressure. More specifically, the inner compartment may comprise at least one sheet whose edges are welded or bonded. When such an inner compartment is formed of a single sheet, it is folded on itself and the edges facing each other are sealed together. A sheet such as this may include a layer of appropriate material, for example, thermoplastic, or be formed of a multilayer complex sheet. In another aspect, the inner compartment is formed of two superposed sheets, for example, rectangular, sealed together around their entire periphery. Alternatively, it is possible to perform this sealing in a perforated way, for example, producing a goffered structure.

After the contents of the outer compartment 20 and inner compartment 30 are combined, an access opening 70 is formed in the outer compartment 20 in order to permit the user to have access to the ascorbic acid carrier composition 28 formed in the device 10. The access opening 70 may be formed simply by manually tearing or cutting the outer compartment. A tear notch 72 is preferably formed in the outer compartment 20 in order to facilitate tearing the outer compartment 20 at a predetermined location. Alternatively, the access opening may be formed by forming a declivity, score line, or frangible seal in the outer compartment as discussed above.

Figure 6A:
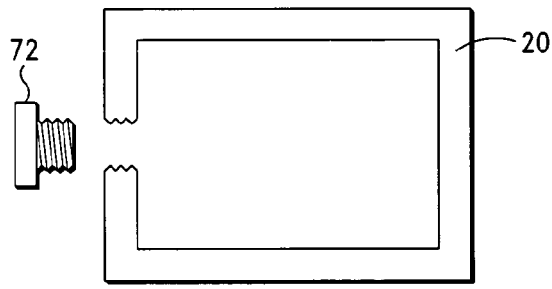
FIG. 6A shows a removable cap overlying an opening formed in the outer compartment in order to provide access to the contents of the device
Figure 6B:
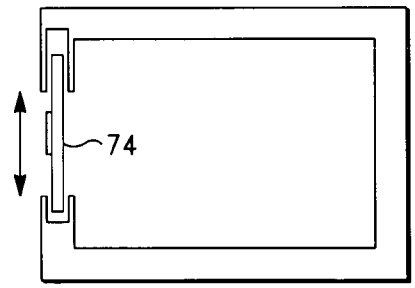
FIG. 6B shows a slideable gate formed in the outer compartment in order to provide access to the contents of the device.
Figure 6C:
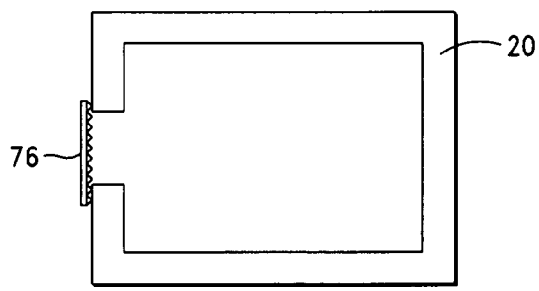
FIG. 6C shows a self-adhesive sticker overlying an opening formed in the outer compartment in order to provide access to the contents of the device.

The outer compartment 20 may also include a cap or gate over the access opening 70 so that the contents of the device 10 may be rescaled in the event that not all of the ascorbic acid carrier composition 28 is used by the patient. As shown in FIG. 6A, a removable cap 72 is threaded and engages corresponding threads 78 in the outer compartment 20. Alternatively, as shown in FIG. 6B, a slideable gate 74 is formed in the outer compartment 20. In FIG. 6C, the opening 70 is reversibly closed by a self-adhesive sticker 76, which the user removes in order to open the device 10 and then repositions sticker 76 after use in order to close the outer compartment again.

The outer compartment 20 and/or the inner compartment 30 may optionally have an absorbent material 60 positioned therein. The absorbent material is of a known type, including but not limited to cotton fibers or synthetic fibers, such as plastic fibers, or a semi-porous material, such as a sponge, hydrogel, collagen, and hydrocolloid laminates. Thus, the absorbent material may include woven material, a nonwoven material, an open-cell foam, a semi-open-cell foam, a felt, and a laminate. The absorbent material may be in the form of a wipe, a patch, a pad, or a mask.

The absorbent material may be coupled to said outer compartment or the inner compartment, for example by using an appropriate adhesive or through the surface tension (e.g., in the case of a laminate) or adhesive properties of the laminate. Alternatively, the absorbent material may be freely disposed within one of the compartments.

When the absorbent material is positioned in the compartment containing the solid vitamin-containing composition comprising ascorbic acid or its pharmaceutically acceptable salts and esters, the absorbent material is preferably impregnated with the solid active agent. When the absorbent material is positioned in the compartment containing the carrier system, preferably at least some of the carrier system flows into the absorbent material.

The outer compartment 20 and/or the inner compartment 30 may optionally have an abrasive material 70 positioned therein. The abrasive material 70 is such that the rubbing against the skin will cause significant exfoliation. Abrasion of the outer layer or epidermis (stratum corneum) of the skin is desirable to smooth or blend scars, blemishes, or other skin conditions that may be caused by, for example, acne, sun exposure, and aging. In addition, abrasion of the skin also facilitates the transdermal delivery of the ascorbic acid carrier composition 28 to the skin. The abrasion also triggers the degranulation of mast cells to trigger the inflammatory phase of healing.

The abrasive material may be coupled to said outer compartment or the inner compartment, for example by using an appropriate adhesive or through the surface tension or adhesive properties of the laminate. Alternatively, the abrasive materially may be freely disposed within one of the compartments. In addition, the abrasive material may be bonded or otherwise adhered to the absorbent material as generally shown in FIG. 1A. The abrasive material may also be impregnated into the absorbent material.

A commercially available uniform, lofty, open, non-woven, three-dimensional, lightweight abrasive web material is available from the Minnesota Mining and Manufacturing ("3M") Company and is sold for commercial and industrial applications under the trade name Scotch-Brite, as described in Hoover et al., U.S. Pat. No. 2,958,593, and Klecker et al., U.S. Pat. No. 4,078,340, and Heyer et al., U.S. Pat. No. 5,363,604, the entire disclosures of which are incorporated herein by reference. Specific reference is made to the photograph of FIG. 1 in U.S. Pat. No. 2,958,593, illustrating the globules of binder carrying abrasive particles and showing the open, lofty structure defining the voids between the filaments in the structure which the applicant has discovered is so well suited to gently abrading and exfoliating the epidermis and accumulating the detritus from the horny corneal layer of the over skin. Other exemplary abrasive materials include, but are not limited to, silica sand, aluminum oxide (corundum), pumice, rouge (iron oxide), feldspar, silicon carbide, boron carbide, cerium oxide, quartz, garnet, titanium dioxide, calcium carbonate, calcium phosphate, diatomaceous earth, perlite, kaolin, mica, tripoli, rigid polymeric materials, talc, vermiculite, water absorbent soft abrasives, and combinations thereof. An abrasive material 70 (e.g., sandpaper) may be bonded to at least a portion of the absorbent material 60. The sandpaper may have a larger or smaller grain size depending upon the degree of exfoliation desired. The abrasive material may also be impregnated in the laminate matrix.

To activate and use the device 10, the user first squeezes or bends the outer compartment 20 so as to apply a compressive or bending force against the inner compartment 30, thereby creating one or more openings 40 in the inner compartment 20. Such bending/compressive forces cause the inner compartment to rupture, the breakable barrier to break, or the puncture tips to puncturely engage the inner compartment, etc. The contents of the outer compartment and the inner compartment are then mixed together. Typically, the carrier system 35 readily flows into the other compartment through the openings; however, manual manipulation of the compartment contents may be used to facilitate mixing of the compartments. The vitamin-containing composition 25 comprising ascorbic acid or its pharmaceutically acceptable salts and esters is hydrated or otherwise solubilized with the carrier system to form an ascorbic acid carrier composition 28. The ascorbic acid carrier composition 28 may be transferred back and forth between the compartments 20, 30 by the user (e.g., by shaking or otherwise moving the device) to ensure that the entire volume of the carrier system 35 has been mixed with the vitamin-containing composition 25 comprising ascorbic acid or its pharmaceutically acceptable salts and esters.

Once the contents of the first compartment and second compartment have been mixed to form the ascorbic acid carrier composition 28, the composition 28 may be directly applied to the user's skin. For devices having an absorbent material 60, the ascorbic acid carrier composition 28 is preferably applied to the absorbent material 60. To enhance delivery, the epidermis of the subject may be abraded using the optional abrasive material 70. The user preferably abrades the skin just prior to application of the ascorbic acid carrier composition 28, e.g., typically within 10 minutes prior to application. In addition or alternatively, the user may abrade the skin simultaneously with application of the ascorbic acid carrier composition 28 to the skin if the an absorbent material with the ascorbic acid carrier composition includes an abrasive surface.

It will be appreciated that the multiple compartment ascorbic acid delivery unit can form part of a kit. The kit comprises the combination of (1) a multiple-compartment ascorbic acid unit as described herein; and (2) a set of instructions for combining the contents of the first and second compartments together. For example, the instructions may direct the user to apply pressure to a certain area on the outer compartment, break the breakable barrier (or engage the puncture tips), mix the solid vitamin-containing composition and the pharmaceutically acceptable carrier system together to form an ascorbic acid carrier composition, and transfer the ascorbic acid carrier composition to an intended surface.

The multiple compartment ascorbic acid delivery kit may optionally comprise an absorbent material. The set of instructions preferably comprise directions to absorb the ascorbic acid carrier composition with the absorbent material in order to transfer the ascorbic acid carrier composition to the intended surface.

The multiple compartment ascorbic acid delivery kit comprises an abrasive material. The set of instructions further comprise directions to abrade the intended surface with the abrasive material prior to or simultaneously with the transfer of the ascorbic acid carrier composition to the intended surface.

From the foregoing it will be seen that this invention is one well adapted to attain all ends and objectives herein above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims, further, it will be understood that certain features and subcombinations are of utility and may be employed without reference to other features and subcombinations. This is contemplated by and is within the scope of the claims.

The invention claimed is:

1. A multiple-compartment ascorbic acid delivery unit comprising:
   an outer compartment containing a solid vitamin-containing composition comprising ascorbic acid or its pharmaceutically acceptable salts and esters, wherein said outer compartment is impermeable to oxygen and ultraviolet light;
   an inner compartment containing a pharmaceutically acceptable carrier system, wherein said inner compartment is liquid impermeable, wherein said inner compartment is entirely enclosed within said outer compartment; and
   an absorbent structure selected from the group consisting of a wipe, a patch, a pad, and a mask, said absorbent structure located within said outer compartment or said inner compartment, and wherein said absorbent structure is adapted to absorb and transfer an ascorbic acid carrier composition comprising a mixture of said solid vitamin-containing composition and said pharmaceutically acceptable carrier system to an intended surface;
   wherein said inner compartment includes a breakable barrier integrally formed therein such that when said breakable barrier is broken said vitamin-containing composition and said pharmaceutically acceptable carrier system are capable of being combined to form said ascorbic acid carrier composition;
   wherein said outer compartment includes a marking corresponding to said breakable barrier for applying pressure to said outer compartment at a predetermined location in order to break said breakable barrier.

2. The delivery unit of claim 1, wherein said breakable barrier comprises a declivity, score line, or frangible seal in said inner compartment.

3. The delivery unit of claim 1, wherein said outer compartment is comprised of a material selected from the group consisting of a deformable metal or polymer, aluminized or metalized polymer, polycarbonate, polyethylene, vinyl, and polyethylene terephthalate polyester film.

4. The delivery unit of claim 1, wherein said outer compartment further comprises a gated opening having an open position and a closed position, wherein when said gated opening is in said open position said ascorbic acid carrier composition can pass through said gated opening and when said gated opening is in said closed position said ascorbic acid carrier composition remains confined within said outer compartment.

5. The delivery unit of claim 1, wherein said absorbent structure is selected from the group consisting of a woven material, a nonwoven material, an open-cell foam, a semi-open-cell foam, felt, and hydrogel, collagen, and hydrocolloid laminates.

6. The delivery unit of claim 5, wherein said absorbent structure is enclosed within said outer compartment, and wherein said absorbent structure is coupled to said outer compartment.

7. The delivery unit of claim 5, wherein said absorbent structure is enclosed within said outer compartment, and wherein said absorbent structure is impregnated with said solid vitamin-containing composition comprising ascorbic acid or its pharmaceutically acceptable salts and esters.

8. The delivery unit of claim 5, wherein said absorbent structure is enclosed within said inner compartment, and wherein said absorbent structure is coupled to said inner compartment.

9. The delivery unit of claim 5, wherein said absorbent structure has an abrasive material on at least a portion of its surface or said abrasive material is impregnated within said absorbent structure.

10. The delivery unit of claim 1, wherein said outer compartment further includes a means for exposing said ascorbic acid carrier composition to the environment.

11. The delivery unit of claim 10, wherein said means for exposing said ascorbic acid carrier composition comprises at least one tear notch, whereby said at least one tear notch allows a user to tear away a portion of said outer compartment.

12. The delivery unit of claim 10, wherein said means for exposing said ascorbic acid carrier composition comprises a frangible seal formed in said outer compartment.

13. The delivery unit of claim 1, wherein said pharmaceutically acceptable carrier system comprises water.

14. The delivery unit of claim 13, wherein said pharmaceutically acceptable carrier system further comprises one or more organic solvents miscible with water.

15. The delivery unit of claim 13, wherein said pharmaceutically acceptable carrier system further comprises one or more therapeutic agents, chelators, or pH regulators.

16. The delivery unit of claim 1, wherein said pharmaceutically acceptable carrier system comprises one or more therapeutic agents selected from the group consisting of antioxidants, growth factors, hormones, growth inhibitors, vitamins, exfoliators, skin toners, lubricants, hydrators, muscle relaxers, muscle toners, and skin protectors.

17. The delivery unit of claim 1, wherein said solid vitamin-containing composition comprises at least two solid antioxidants.

18. A multiple-compartment ascorbic acid delivery unit comprising:
an outer compartment containing a pharmaceutically acceptable carrier system, wherein said outer compartment is liquid impermeable, wherein said outer compartment is impermeable to oxygen and ultraviolet light;
an inner compartment containing a solid vitamin-containing composition comprising ascorbic acid or its pharmaceutically acceptable salts and esters, wherein said inner compartment is entirely enclosed within said outer compartment;
an absorbent structure comprising a hydrogel or hydrocolloid laminate selected from the group consisting of a wipe, a patch, a pad, and a mask, said absorbent structure located within said inner compartment or said outer compartment, and wherein said absorbent structure is adapted to absorb and transfer an ascorbic acid carrier composition comprising a mixture of said solid vitamin-containing composition and said pharmaceutically acceptable carrier system to an intended surface;
wherein said inner compartment includes a means for combining said solid vitamin-containing composition and said pharmaceutically acceptable carrier system to form said ascorbic acid carrier composition, and wherein said means for combining comprises a breakable barrier integrally formed in said inner compartment such that when said breakable barrier is broken said vitamin-containing composition and said pharmaceutically acceptable carrier system are capable of being combined to form said ascorbic acid carrier composition; and
wherein said outer compartment includes a marking thereon for applying pressure to said outer compartment at a predetermined location in order to break said breakable barrier.

19. The delivery unit of claim 18, wherein said breakable barrier comprises a declivity, score line, or frangible seal in said inner compartment.

20. The delivery unit of claim 18, wherein said inner compartment is comprised of a material selected from the group consisting of a deformable metal or polymer, aluminized or metalized polymer, polycarbonate, polyethylene, vinyl, and polyethylene terephthalate polyester film.

21. The delivery unit of claim 18, wherein said outer compartment further comprises a gated opening having an open position and a closed position, wherein when said gated opening is in said open position said ascorbic acid carrier composition can pass through said gated opening and when said gated opening is in said closed position said ascorbic acid carrier composition remains confined within said outer compartment.

22. The delivery unit of claim 18, wherein said absorbent structure is coupled to said outer compartment.

23. The delivery unit of claim 18, wherein said absorbent structure has an abrasive material on at least a portion of its surface or said abrasive material is impregnated within said absorbent structure.

24. The delivery unit of claim 18, wherein said outer compartment includes a means for exposing said ascorbic acid carrier composition to the environment.

25. The delivery unit of claim 24, wherein said means for exposing said ascorbic acid carrier composition comprises at least one tear notch, whereby said at least one tear notch allows a user to tear away a portion of said outer compartment.

26. The delivery unit of claim 24, wherein said means for exposing said ascorbic acid carrier composition comprises a frangible seal formed in said outer compartment.

27. The delivery unit of claim 18, wherein said pharmaceutically acceptable carrier system comprises water.

28. The delivery unit of claim 27, wherein said pharmaceutically acceptable carrier system further comprises one or more organic solvents miscible with water.

29. The delivery unit of claim 27, wherein said pharmaceutically acceptable carrier system further comprises one or more therapeutic agents, chelators, or pH regulators.

30. The delivery unit of claim 27, wherein said pharmaceutically acceptable carrier system comprises one or more therapeutic agents selected from the group consisting of antioxidants, growth factors, hormones, growth inhibitors, vitamins, exfoliators, skin toners, lubricants, hydrators, muscle relaxers, muscle toners, and skin protectors.

31. The delivery unit of claim 18, wherein said solid vitamin-containing composition comprises at least two solid antioxidants.

32. A multiple compartment ascorbic acid delivery kit, said kit comprising the combination of:
a multiple-compartment ascorbic acid delivery unit according to claim 1; and
a set of instructions for breaking said breakable barrier, mixing said solid vitamin-containing composition and said pharmaceutically acceptable carrier system together to form said ascorbic acid carrier composition, and transferring said ascorbic acid carrier composition to said intended surface.

33. The multiple compartment ascorbic acid delivery kit of claim 32 wherein said set of instructions further comprise absorbing said ascorbic acid carrier composition with said absorbent material in order to transfer said ascorbic acid carrier composition to said intended surface.

34. The multiple compartment ascorbic acid delivery kit of claim 32 further comprising an abrasive material, and wherein said set of instructions further comprise abrading said intended surface with said abrasive material prior to or simultaneous with said transferring.

35. The multiple compartment ascorbic acid delivery kit of claim 32, wherein said pharmaceutically acceptable carrier system comprises one or more therapeutic agents selected from the group consisting of antioxidants, growth factors, hormones, growth inhibitors, vitamins, exfoliators, skin toners, lubricants, hydrators, muscle relaxers, muscle toners, and skin protectors in said carrier system.

36. The multiple compartment ascorbic acid delivery kit of claim 32, wherein said solid vitamin-containing composition further comprises at least two solid antioxidants.

\* \* \* \* \*